United States Patent
Han et al.

(10) Patent No.: US 10,329,288 B2
(45) Date of Patent: Jun. 25, 2019

(54) PROCESS FOR PREPARING A COMPOUND

(71) Applicants: Genentech, Inc., South San Francisco, CA (US); Array BioPharma Inc., Boulder, CO (US)

(72) Inventors: Chong Han, South San Francisco, CA (US); Keena Green, South San Francisco, CA (US); Francis Gosselin, South San Francisco, CA (US); Michelangelo Scalone, Birsfelden (CH); Paul J. Nichols, Boulder, CO (US); Weidong Liu, Boulder, CO (US); Keith L. Spencer, Boulder, CO (US); Zackary D. Crane, Boulder, CO (US); Peter J. Stengel, Boulder, CO (US); Sagar Shakya, Boulder, CO (US)

(73) Assignees: Genentech, Inc., South San Francisco, CA (US); Array BioPharma Inc., Boulder, CO (US)

( * ) Notice: Subject to any disclaimer, the term of this patent is extended or adjusted under 35 U.S.C. 154(b) by 0 days.

(21) Appl. No.: 14/913,635

(22) PCT Filed: Aug. 21, 2014

(86) PCT No.: PCT/US2014/052146
§ 371 (c)(1),
(2) Date: Feb. 22, 2016

(87) PCT Pub. No.: WO2015/027092
PCT Pub. Date: Feb. 26, 2015

(65) Prior Publication Data
US 2016/0200723 A1 Jul. 14, 2016

Related U.S. Application Data

(60) Provisional application No. 61/868,933, filed on Aug. 22, 2013.

(51) Int. Cl.
*C07D 471/04* (2006.01)

(52) U.S. Cl.
CPC ................... *C07D 471/04* (2013.01)

(58) Field of Classification Search
CPC .................................... C07D 471/04
USPC ........................................ 546/113
See application file for complete search history.

(56) References Cited

U.S. PATENT DOCUMENTS

| 2011/0070317 | A1 | 3/2011 | Le Huerou et al. |
| 2011/0086835 | A1* | 4/2011 | Rodgers ............... C07D 487/04 514/210.18 |
| 2013/0045286 | A1* | 2/2013 | Le Huerou .......... C07D 471/04 424/649 |

FOREIGN PATENT DOCUMENTS

| WO | 1996036597 A1 | 11/1996 |
| WO | 0200661 A1 * | 1/2002 |
| WO | 2002000661 A1 | 1/2002 |
| WO | 2003028724 A1 | 4/2003 |
| WO | 2005063746 A1 | 3/2005 |
| WO | 2005095358 A2 | 10/2005 |
| WO | 2006091568 A2 | 8/2006 |
| WO | 2007007919 A2 | 1/2007 |
| WO | 2009089352 | * 7/2009 |
| WO | 2009089352 A1 | 7/2009 |
| WO | 2009089359 A1 | 7/2009 |
| WO | 2009140320 A1 | 11/2009 |
| WO | 2013024898 A1 | 2/2013 |
| WO | 2013114113 A1 | 8/2013 |

OTHER PUBLICATIONS

Ahn, et al., "The Chk2 protein kinase", DNA Repair 3, 1039-1047 (2004).
Bartek, et al., "CHK2 kinase—a busy messenger", Nat. Rev. Mol. Cell Biol. 2 (12), 877-886 (2001).
Janetka, et al., "Inhibitors of checkpoint kinases: from discovery to the clinic", Drug Discovery and Development vol. 10 (4), 473-486 (2007).
Patent Cooperation Treaty, International Searching Authority, Search Report and Written Opinion for PCT/US2014/52146, 9 pages, Nov. 6, 2014.
Pommier, et al., "Targeting chk2 kinase: molecular interaction maps and therapeutic rationale", Current Pharmaceutical Design, vol. 11 (22), 2855-2872 (2005).
Tse, et al., Clinical Cancer Research, 13, 1955-1960 (2007).
Terrier, "Synthetic Aspects of Intermolecular SnAr Reactions", Modern Nucleophilic Aromatic Substitution, First Edition, John Wiley & Sons, Inc., 205-278 (2013).

* cited by examiner

*Primary Examiner* — Taofiq A Solola
(74) *Attorney, Agent, or Firm* — Viksnins Harris Padys Malen LLP

(57) ABSTRACT

The invention provides processes of preparation thereof useful in the preparation of compounds that can be used as CHK1 inhibitors.

20 Claims, No Drawings

PROCESS FOR PREPARING A COMPOUND

RELATED APPLICATIONS

This patent application claims the benefit of priority of U.S. application Ser. No. 61/868,933, filed Aug. 22, 2013, which application is herein incorporated by reference.

FIELD OF THE INVENTION

In an aspect, the present invention relates to a process for making a compound with anti-cancer activity, for example a compound which inhibits CHK1 kinase activity.

BACKGROUND OF THE INVENTION

Protein kinases are kinase enzymes that phosphorylate other proteins. The phosphorylation of these proteins usually produces a functional change in the protein. Most kinases act on serine and threonine or tyrosine, and some kinases act on all three. Through these functional changes, kinases can regulate many cellular pathways. Protein kinase inhibitors are compounds that inhibit these protein kinases, and thus can be used to affect cellular pathways.

Checkpoint kinase 1 ("CHK1") is a serine/threonine kinase. CHK1 regulates cell-cycle progression and is a main factor in DNA-damage response within a cell. CHK1 inhibitors have been shown to sensitize tumor cells to a variety of genotoxic agents, such as chemotherapy and radiation. (Tse, Archie N., et al., "Targeting Checkpoint Kinase 1 in Cancer Therapeutics." Clin. Cancer Res. 13(7) (2007) 1955-1960). It has been observed that many tumors are deficient in the G1 DNA damage checkpoint pathway, resulting in the reliance on S and G2 checkpoints to repair DNA damage and survive. (Janetka, James W., et al., "Inhibitors of checkpoint kinases: From discovery to the clinic." Drug Discovery & Development Vol. 10, No. 4 (2007) 473-486).

The S and G2 checkpoints are regulated by CHK1. Inhibition of CHK1 has been shown to cancel the S and G checkpoints, thereby impairing DNA repair and resulting in increased tumor cell death. However, non-cancerous cells have a functioning G checkpoint, allowing for DNA repair and survival.

Checkpoint kinase 2 ("CHK2") is also a serine/threonine kinase. CHK2's functions are central to the induction of cell cycle arrest and apoptosis by DNA damage. (Ahn, Jinwoo, et al., "The CHK2 protein kinase." DNA Repair 3 (2004) 1039-1047). CHK2 is activated in response to genotoxic insults and propagates the checkpoint signal along several pathways, which eventually causes cell-cycle arrest in the G1, S and G2/M phases, activation of DNA repair, and apoptotic cell death. (Bartek, Jiri, et al., "CHK2 Kinase—A Busy Messenger." Nature Reviews Molecular Cell Biology. Vol. 2(12) (2001) 877-886). Cancer cells often lack one or more genome-integrity checkpoints, so inhibition of CHK2 could make tumor cells selectively more sensitive to anti-cancer therapies, such as γ-radiation or DNA-damaging drugs.

Normal cells would still activate other checkpoints and recover, while cancer cells deprived of checkpoints would be more likely to die. It has been demonstrated that a peptide-based inhibitor of CHK2 abrogated the G2 checkpoint and sensitized p53-defective cancer cells to DNA damaging agents. (Pommier, Yves, et al., "Targeting CHK2 Kinase: Molecular Interaction Maps and Therapeutic Rationale." Current Pharmaceutical Design. Vol. 11, No. 22 (2005) 2855-2872).

CHK1 and/or CHK2 inhibitors are known, see for example, International Publication WO 2009/089352, WO2009/089359 and WO2009/140320.

SUMMARY OF THE INVENTION

An aspect of the invention relates to a process for preparing (R)-5-bromo-4-(3-(amino)piperidin-1-yl)-3-(cyclopropanecarboxamido)-1H-pyrrolo[2,3-b]pyridine of Formula (I):

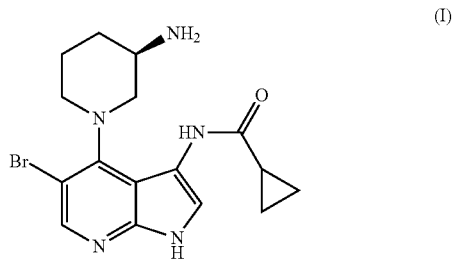 [SMILES: N[C@@H]1CCCN(c2c(Br)cnc3[nH]cc(NC(=O)C4CC4)c23)C1]

and pharmaceutically acceptable salts thereof. (R)-5-bromo-4-(3-(amino)piperidin-1-yl)-3-(cyclopropanecarboxamido)-1H-pyrrolo[2,3-b]pyridine of Formula (I) can be used as a CHK1 inhibitor.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. The invention is intended to cover all alternatives, modifications, and equivalents which may be included within the scope of the present invention. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The words "comprise" "comprising" "include" "including" and "includes" when used in this specification and in the following claims are intended to specify the presence of stated features, integers, components, or steps, but they do not preclude the presence or addition of one or more other features, integers, components, steps, or groups thereof.

The term "about" when used in conjunction with hours, temperatures denotes ±5 hours, for example ±1 hour. The term "about" when used in conjunction with temperatures, temperatures denotes ±5 Celsius degrees, for example ±1 Celsius degree. The term "about" when used in conjunction with percentages or other values, temperatures denotes ±10%, for example ±5% to percentage or values it refers to.

The terms "treat" or "treatment" refer to therapeutic, prophylactic, palliative or preventative measures. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

The expressions "therapeutically effective amount" or "effective amount" mean an amount of a compound of Formula I that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by abnormal or unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer (including small-cell lung cancer, non-small cell lung cancer ("NSCLC"), adenocarcinoma of the lung and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer, including melanoma, as well as head and neck cancer.

The expression "pharmaceutically acceptable" indicates that the substance or composition is compatible chemically and/or toxicologically, with the other ingredients comprising a formulation, and/or the mammal being treated therewith.

The expression "pharmaceutically acceptable salt," as used herein, refers to pharmaceutically acceptable organic or inorganic salts of a compound of the invention.

The compounds of this invention also include other salts of such compounds which are not necessarily pharmaceutically acceptable salts, and which may be useful as intermediates for preparing and/or purifying compounds of this invention and/or for separating enantiomers of compounds of this invention.

The term "mammal" means a warm-blooded animal that has or is at risk of developing a disease described herein and includes, but is not limited to, guinea pigs, dogs, cats, rats, mice, hamsters, and primates, including humans.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of of Formulas I to VII described herein may contain asymmetric or chiral centers, and therefore exist in different stereoisomeric forms. It is intended that all stereoisomeric forms of the compounds of Formulas I to VII described herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The expression "pharmaceutically acceptable salt" as used herein, refers to pharmaceutically acceptable organic or inorganic salts of a compound of Formulas I to VII described herein. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, ethanedisulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If a compound of Formulas I to VII described herein is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as benzenesulfonic acid, p-toluenesulfonic acid, methanesulfonic acid, ethanesulfonic acid, or ethanedisulfonic acid, or the like.

If a compound of Formulas I to VII described herein is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association or complex of one or more solvent molecules and a compound of Formulas I to VII described herein. Examples of solvents that form solvates include, but are not limited to, water, 1-propanol, 2-propanol, 1-pentanol, ethanol, methanol, DMSO, ethyl acetate, ethyl formate, acetic acid, toluene, anisole, pyridine, 1,3-diisopropylbenzene, 2-methyltetrahydrofuran, tetrahydrofuran, dioxane, cyclpentyl methyl ether, methyl tert-butyl ether, dichloromethane, 1,2-dichloroethane, methylcyclohexane, acetonitrile, valeronitrile, and ethanolamine. The term "hydrate" refers to the complex where the solvent molecule is water.

CHK1/2 INHIBITORS

The process according to the invention can be useful in the preparation of (R)-5-bromo-4-(3-(amino)piperidin-1-yl)-3-(cyclopropanecarboxamido)-1H-pyrrolo[2,3-b]pyridine of Formula (I), and pharmaceutical formulations thereof, that inhibit CHK1 and/or CHK2 such as for example described in WO2009/140320. This compound is potentially useful in the treatment of diseases, conditions and/or disorders modulated by CHK1 and/or CHK2.

PREPARATION OF COMPOUNDS

The compounds described herein may contain asymmetric or chiral centers, and therefore exist in different stereoisomeric forms. It is intended that all stereoisomeric forms of the compounds of Formulas I to VII described herein, including but not limited to, diastereomers, enantiomers and atropisomers, as well as mixtures thereof such as racemic mixtures, form part of the present invention. In addition, the present invention embraces all geometric and positional isomers. In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds described herein may exist in unsolvated as well as solvated forms with pharmaceutically acceptable solvents such as water, ethanol, and the like, and it is intended that the invention embrace both solvated and unsolvated forms.

The compounds described herein may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present described herein also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^{3}H$ and $^{14}C$) are useful in compound and/or substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

Starting materials and reagents for the preparation of compounds according to the invention are generally available from commercial sources such as Sigma-Aldrich Chemical (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen*

Chemie, 4, Aufl. ed. Springer-Verlag, Berlin, including supplements (also available via the Beilstein online database).

As mentioned above, in one aspect, the invention relates to a process for preparing (R)-5-bromo-4-(3-amino)piperidin-1-yl)-3-(cyclopropanecarboxamido)-1H-pyrrolo[2,3-b]pyridine of Formula (I):

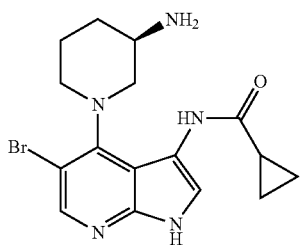

(I)

comprising the step of reacting a compound of Formula (II):

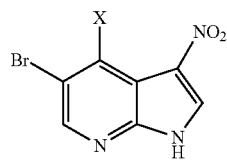

(II)

wherein X is halogen, with a compound of Formula (III):

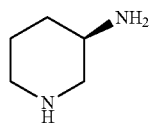

(III)

wherein R is an amino protecting group, to provide a compound of Formula (IV):

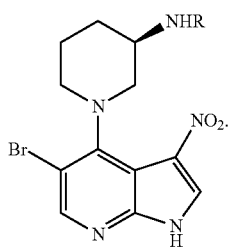

(IV)

In an embodiment, the compound of Formula (II) is reacted at about 1.0 to about 3.0 equivalents of the compound of Formula (III). In one embodiment the reaction between the compound of Formula (II) and of Formula (III) is performed at a temperature above room temperature. In one embodiment the reaction is performed at a temperature above 50° C. In one embodiment the reaction is performed at about 85° C.

In an embodiment, X is I, Cl, F or Br. In an embodiment, X is Cl, F or Br. In an embodiment, X is I. In an embodiment, X is F. In an embodiment, X is Cl. In an embodiment, X is Br.

In an embodiment, the compound of Formula (II) is a compound of Formula (II-a):

(II-a)

In an embodiment, the compound of Formula (II) is a compound of Formula (II-b):

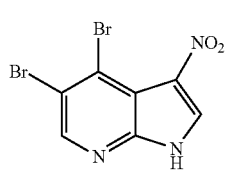

(II-b)

In an embodiment, the compound of Formula (II) is a compound of Formula (II-c):

(II-c)

In an embodiment, the reaction of compound of Formula (II) with compound of Formula (III) described above is performed in an organic solvent or a solvent mixture. In an embodiment, the organic solvent is selected from the group consisting of alcohols, dimethyl sulfoxide (DMSO), dimethylformamide (DMF), dimethylacetamide (DMA), N-methyl-2-pyrrolidone (NMP), sulfolane, acetonitrile, and propionitrile. In an embodiment, the alcohol is selected from the group consisting of as 2-methyl-2-butanol, 1-butanol, 2-butanol, 2-methyl-2-propanol, 1-propanol and 2-propanol. In an embodiment the alcohol is 2-methyl-2-butanol.

In an embodiment, the reaction of compound (II) with compound (III) described above is performed with a base selected from the group consisting of N-methymorpholine, 1,4-diazabicyclo[2.2.2]octane (DABCO), triethylamine, N,N-diisopropylethylamine (DIEA), tetramethylethylenediamine (TMEDA), sodium carbonate, potassium carbonate, cesium carbonate, and potassium phosphate. In an embodiment the base is N-methylmorpholine.

In an embodiment, the amino protecting group R is selected from the group consisting of: triphenylmethyl (trityl), tert-butyloxycarbonyl (Boc), carboxybenzyl (Cbz), trifluoroacetyl and acetyl.

In an embodiment, the process of the invention further comprises the step of subjecting the compound of Formula (IV):

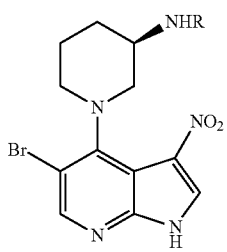

(IV)

wherein R is an amino protecting group, to a nitro reduction to obtain a compound of Formula (V):

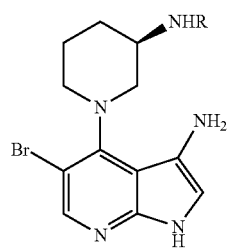

(V)

In an embodiment, the nitro reduction step is performed using hydrogen, sulfide, or borane as the reductant. In an embodiment, the hydrogenation is performed with a platinum or Raney nickel catalyst. In an embodiment, the catalyst is used in conjunction with a modifier selected from the group consisting of vanadium, iron and copper. In an embodiment, the hydrogetation step is performed with a base selected from the group consisting of N-methymorpholine, 1,4-diazabicyclo[2.2.2]octane (DABCO), triethylamine, N,N-diisopropylethylamine (DIEA), tetramethylethylenediamine (TMEDA). In an embodiment, the hydrogenation step is performed in a solvent selected from 2-methyl-2-butanol, 1-butanol, 2-butanol, 2-methyl-2-propanol, 1-propanol, 2-propanol, 2-methyltetrahydrofuran, and tetrahydrofuran. In an embodiment, the hydrogenation step is performed at 5 bar of hydrogen.

In an embodiment, the process of the invention further comprises the step of reacting a compound of Formula (V):

(V)

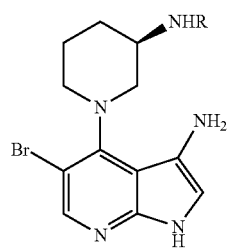

with a compound of Formula (VI):

(VI)

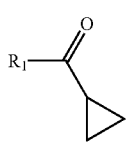

wherein $R^1$ is selected from the group consisting of chlorine, fluorine, bromine, and $OR^2$, wherein $R^2$ is selected from the group consisting of cyclopropylcarbonyl, isobutylcarbonyl, isopropylcarbonyl, ethylcarbonyl, methylcarbonyl, 2-pyridyl, N-succinimidal, etc. to obtain a compound of Formula (VII):

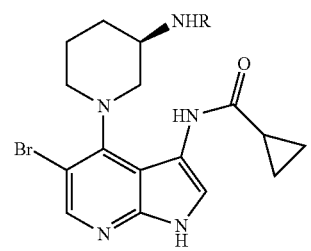

(VII)

In an embodiment, the process of the invention further comprises the step of removing protecting group R in the compound of Formula (VII):

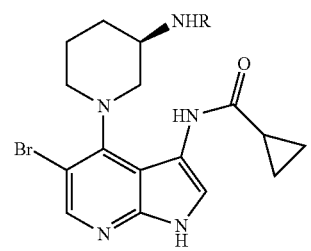

(VII)

to obtain (R)-5-bromo-4-(3-(amino)piperidin-1-yl)-3-(cyclopropanecarboxamido)-1H-pyrrolo[2,3-b]pyridine of Formula (I):

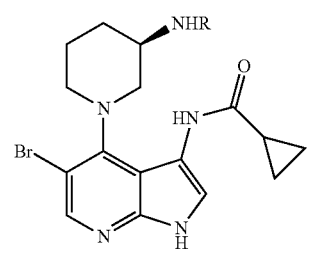

(I)

In an embodiment, the amino protecting group R is tert-butyloxycarbonyl (Boc). In this case, deprotection thereof can be performed under acidic conditions using sulfuric acid, hydrochloric acid, or trifluroacetic acid. The freebase form can be obtained by treating the salt with an inorganic base such as sodium hydroxide, potassium hydroxide, or potassium phosphate or an organic base such as piperizine, piperidine, pyrrolidine, 1,4-diazabicyclo[2.2.2]octane (DABCO), triethylamine, N,N-diisopropylethylamine (DIEA), or tetramethylethylenediamine (TMEDA). In an embodiment, the base is piperazine.

A person skilled in the art will recognize that the conditions and reagents of schemes 2, 3, 4 and 5 of WO2009140320, the content of which is incorporated by reference, can also be applied to the above process in the preparation of a compound of Formula (I).

METHODS OF SEPARATION

In the methods of preparing the compounds of Formulas I to VII described herein, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of Formulas I to VII described herein may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the of Formulas I to VII described herein can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem., (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

ADMINISTRATION AND PHARMACEUTICAL FORMULATIONS

The compound of Formula (I) may be administered by any convenient route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compound may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion.

A typical formulation is prepared by mixing a compound of Formula (I) and a carrier or excipient. Suitable carriers and excipients are well known to those skilled in the art and are described in detail in, e.g., Ansel, Howard C., et al.,

*Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of Formula (I) or pharmaceutical composition thereof) or aid in the manufacturing of the pharmaceutical product (i.e., medicament).

One embodiment includes a pharmaceutical composition comprising a compound of Formula (I), or pharmaceutically acceptable salt thereof. A further embodiment provides a pharmaceutical composition comprising a compound of Formula (I) or pharmaceutically acceptable salt thereof, together with a pharmaceutically acceptable carrier or excipient.

METHODS OF TREATMENT WITH COMPOUNDS OF FORMULA (I)

The compound of Formula (I) can be used for treating or preventing disease or condition by administering one or more compounds of Formula (I) or pharmaceutically acceptable salt thereof. In one embodiment, a human patient is treated with a compound of Formula (I) or pharmaceutically acceptable salt thereof, and a pharmaceutically acceptable carrier, adjuvant, or vehicle in an amount to detectably inhibit CHK1 activity.

A method of preventing or treating a disease or disorder modulated by CHK1 and/or CHK2 can comprise administering to a mammal in need of such treatment an effective amount of a compound of Formula (I).

In another embodiment a method of treating a hyperproliferative disease in a mammal comprising administering a therapeutically effective amount of the compound of Formula (I) or pharmaceutically acceptable salt thereof, to the mammal is provided.

In another embodiment, a method of treating or preventing cancer, including the below identified conditions, in a mammal in need of such treatment, wherein the method comprises administering to said mammal a therapeutically effective amount of a compound of Formula (I) or pharmaceutically acceptable salt thereof.

In certain embodiments, the CHK1 inhibitor of Formula (I) (i.e., a compound of Formula (I)) is administered in combination with a DNA damaging agent. Generally, the DNA damaging agent will be administered before the CHK1 inhibitor of Formula (I). DNA damaging agents include Gemzar® (gemcitabine), Camptosar® (irinotecan or CPT-11), Temodar® (temozolomide), Xeloda® (capecitabine), Hycamtin® (topotecan), cisplatin, Eloxatin® (oxaliplatin), Paraplatin® (carboplatin), camptothecin, ara-C (cytarabine), 5-FU (fluorouracil), Cytoxan (cyclophosphamide), Etopophos® or Vepesid® (etoposide phosphate), Vumon® (teniposide), Adriamycin PFS® or Adriamycin RDF® (doxorubicin), daunorubicin, Alimta® (pemetrexed), and radiation. In certain embodiments, the DNA damaging agent is selected from the group consisting of gemcitabine, irinotecan, temozolomide, capecitabine, camptothecin, cisplatin, ara-C, and 5-FU. In certain embodiments, the DNA damaging agent is selected from gemcitabine, irinotecan, temozolomide and capecitabine. In certain embodiments, the DNA damaging agent is selected from gemcitabine, irinotecan, cisplatin, oxaliplatin, carboplatin and cytarabine. In certain embodiments, the DNA damaging agent is selected from gemcitabine and irinotecan. The DNA damaging agent is administered at its approved or recommended dose.

Because of the ability of a CHK1 inhibitor to potentiate the activity of many anti-cancer agents it is expected that a wide range of tumor types may be treated by the compositions and methods described herein. These conditions include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Breast: invasive breast carcinomas (invasive ductal carcinoma and invasive lobular carcinoma), etc.; and Adrenal glands: neuroblastoma. The term hyperproliferative disease includes the above identified conditions. The term "cancerous cell" as provided herein, includes a cell afflicted by any one of the above identified conditions.

In certain embodiments herein, the cancer is selected from colorectal cancer (including Ras mutations), small cell lung cancer, non-small cell lung cancer, glioma, ovarian cancer, metastatic breast cancer, pancreatic cancer, hepatobiliary cancer (including hepatocellular cancer, bile duct cancer and cholangiocarcinoma), gastric cancer, testicular cancer, head and neck squamous cell carcinoma, leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostrate cancer.

In certain embodiments herein, the cancer is a solid tumor cancer.

In certain embodiments herein, the cancer is selected from pancreatic cancer, ovarian cancer and colorectal cancer.

In certain embodiments herein, the cancer is selected from colorectal cancer (including Ras mutations), small cell lung cancer, non-small cell lung cancer, and glioma. In certain embodiments, the CHK1 inhibitor is administered in combination with a DNA damaging agent. In a further embodiment, the DNA damaging agent is irinotecan.

In certain embodiments herein, the cancer is selected from non-small cell lung cancer, ovarian cancer, metastatic breast cancer, pancreatic cancer, hepatobiliary cancer (including hepatocellular cancer, bile duct cancer and cholangiocarcinoma), and gastric cancer. In certain embodiments, the CHK1 inhibitor is administered in combination with a DNA damaging agent. In a further embodiment, the DNA damaging agent is gemcitabine.

In certain embodiments herein, the cancer is selected from colorectal cancer (including Ras mutations), small cell lung cancer, non-small cell lung cancer, ovarian cancer, hepatobiliary cancer (including hepatocellular cancer, bile duct cancer and cholangiocarcinoma), gastric cancer, testicular cancer, and head and neck squamous cell carcinoma. In certain embodiments, the CHK1 inhibitor is administered in combination with a DNA damaging agent. In a further embodiment, the DNA damaging agent is selected from the group consisting of cisplatin, oxaliplatin, and carboplatin.

In certain embodiments herein, the cancer is selected from leukemia (including acute myeloid leukemia, acute lymphoblastic leukemia, chronic myeloid leukemia, and chronic lymphoid leukemia), lymphoma (including mantle cell lymphoma, Hodgkin's lymphoma and non-Hodgkin's lymphoma), and prostrate cancer. In certain embodiments, the CHK1 inhibitor is administered in combination with a DNA damaging agent. In a further embodiment, the DNA damaging agent is cytarabine.

Another embodiment herein provides the use of a compound of Formula (I) or a pharmaceutically acceptable salt thereof, in the manufacture of a medicament for the treatment of cancer.

In another embodiment, a method of treating or preventing a disease or disorder modulated by CHK1 and/or CHK2, comprising administering to a mammal in need of such treatment an effective amount of a compound of Formula (I) or a pharmaceutically acceptable salt thereof.

In another embodiment, a method of preventing or treating cancer, comprising administering to a mammal in need of such treatment an effective amount of a compound of Formula (I), alone or in combination with one or more additional compounds having anti-cancer properties.

CHK1 inhibitors are expected to potentiate the activity of a wide range of anti-cancer agents (or DNA damaging agents), when such agent(s) trigger the CHK1 dependent cell cycle checkpoint.

The compound of Formula (I) can be used in a composition for the treatment of a hyperproliferative disease in a mammal, wherein said composition comprises a therapeutically effective amount of a compound of Formula (I) or a pharmaceutically acceptable salt thereof, in combination with an anti-tumor agent selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

The compound of Formula (I) can also be used in a method for the treatment of a hyperproliferative disorder in a mammal that comprises administering to said mammal a therapeutically effective amount of a compound of Formula I or a pharmaceutically acceptable salt thereof, in combination with an anti-tumor agent selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

Another embodiment provides compounds of Formula (I) for use in therapy. In a further embodiment, the use also includes the use of a DNA damaging agent.

Another embodiment provides compounds of Formula (I) for use in the treatment of a hyperproliferative disease. In a further embodiment, the hyperproliferative disease is cancer, including the above identified conditions. In a further embodiment, the use also includes the use of a DNA damaging agent.

The compounds of Formula (I) can be used in a pharmaceutical composition for inhibiting abnormal cell growth in a mammal, which composition comprises an amount of a compound of Formula (I), or a stereoisomer or a pharmaceutically acceptable salt thereof, in combination with an amount of a chemotherapeutic, wherein the amounts of the compound, stereoisomer or salt and of the chemotherapeutic are together effective in inhibiting abnormal cell growth. Many chemotherapeutics are known in the art. In certain embodiments, the chemotherapeutic is selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and/or prenyl-protein transferase inhibitors.

The compound of Formula I can be used in a method for inhibiting abnormal cell growth in a mammal or treating a hyperproliferative disorder, in which the method comprises administering to the mammal an amount of a compound of Formula I, or a pharmaceutically acceptable salt thereof, in combination with radiation therapy, wherein the amounts of the compound or salt, in combination with the radiation therapy is effective in inhibiting abnormal cell growth or treating the hyperproliferative disorder in the mammal. Techniques for administering radiation therapy are known in the art, and these techniques can be used in the combination therapy described herein. The administration of the compound of Formula I in this combination therapy can be determined as described herein.

It is believed that the compound of Formula I can render abnormal cells more sensitive to treatment with radiation for purposes of killing and/or inhibiting the growth of such cells. Accordingly, the compound of Formula I can be used in to a method for sensitizing abnormal cells in a mammal to treatment with radiation, which method comprises administering to the mammal an amount of a compound of Formula I or a stereoisomer or a pharmaceutically acceptable salt thereof, which amount is effective in sensitizing abnormal cells to radiation treatment. The amount of the compound, stereoisomer or salt to be used in this method can be determined according to means for ascertaining effective amounts of such compounds as described herein or by methods know to those skilled in the art.

Another embodiment provides the use of a compound of Formula I, or pharmaceutically acceptable salt thereof, in the manufacture of a medicament for the treatment of hyperproliferative diseases. In a further embodiment, the hyperproliferative disease may be cancer, including the above identified conditions. In a further embodiment, the use also includes the use of a DNA damaging agent.

Another embodiment provides the use of a compound of Formula I, in the manufacture of a medicament, for use as a CHK1 and/or CHK2 inhibitor in the treatment of a patient undergoing cancer therapy, including the above identified conditions, is provided. In a further embodiment, the use also includes the use of a DNA damaging agent.

Another embodiment o provides the use of a compound of Formula I in the treatment of a hyperproliferative disease. In a further embodiment, the hyperproliferative disease is cancer, including the above identified conditions. In a further embodiment, the use also includes the use of a DNA damaging agent.

Another embodiment provides the use of a compound of Formula I in the manufacture of a medicament, for use as a CHK1 and/or CHK2 inhibitor in the treatment of a patient undergoing cancer therapy. In a further embodiment, the use also includes the use of a DNA damaging agent.

In another embodiment, a pharmaceutical composition comprising a compound of Formula I for use in the treatment of a hyperproliferative disease is provided.

In another embodiment, a pharmaceutical composition comprising a compound of Formula I for use in the treatment of cancer is provided.

COMBINATION THERAPY

The compound of Formula (I) described herein and pharmaceutically acceptable salts thereof may be employed alone or in combination with other therapeutic agents for treatment. The compound of Formula (I) can be used in combination with one or more additional drugs, for example an anti-inflammatory compound that works by a different mechanism of action. The second compound of the pharmaceutical combination formulation or dosing regimen preferably has complementary activities to the compound of Formula I such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

EXAMPLES

In order to illustrate the invention, the following example is included. However, it is to be understood that this example does not limit the invention and is only meant to suggest a method of practicing the invention. Persons skilled in the art will recognize that the chemical reactions described may be readily adapted to alternative methods for preparing the compound of this invention which are deemed to be within the scope of this invention.

In the example described below, unless otherwise indicated all temperatures are set forth in degrees Celsius (° C.). Reagents were purchased from commercial suppliers such as Sigma-Aldrich Chemical Company, and were used without further purification unless otherwise indicated.

Example 1

Preparation of (R)-5-bromo-4-(3-amino)piperidin-1-yl)-3-(cyclopropanecarboxamido)-1H-pyrrolo[2,3-b]pyridine

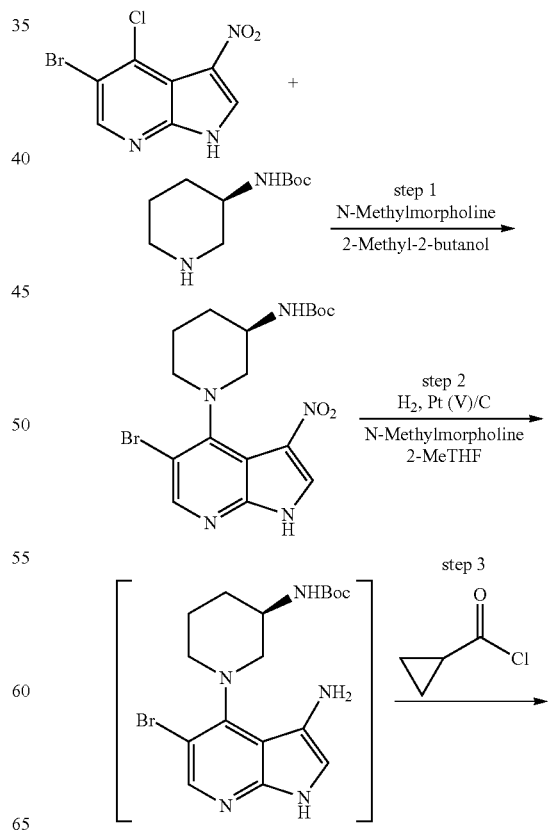

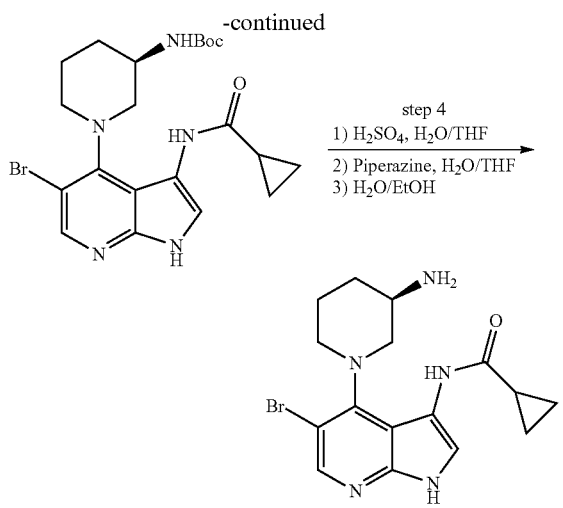

Step 1: Preparation of (R)-5-bromo-4-(3-(tert-butoxycarbonylamino)piperidin-1-yl)-3-nitro-1H-pyrrolo[2,3-b]pyridine To an inserted 10 L jacket reactor, equipped with a mechanic stirrer, a nitrogen/vacuum manifold, a thermocouple, and a condenser, were charged 2-methyl-2-butanol (3.30 L), 5-bromo-4-chloro-3-nitro-1H-pyrrolo[2,3-b]pyridine (330 g, 1.00 equiv), (R)-tert-butyl piperidin-3-ylcarbamate (456 g, 2.00 equiv), and N-methylmorpholine (115 g, 1.00 equiv). The reaction mixture was stirred at 85° C. for 48 h and cooled to 20° C. The mixture was then washed with 15 wt % citric acid aqueous solution (3.30 kg) and water (3.30 kg). The majority of 2-methyl-2-butanol was distilled off under vacuum at 50° C. Acetonitrile was added to bring the mixture back to its original volume. Continuous distillation was conducted until a total of 10.3 kg of acetonitrile was added. Water (3.20 kg) was slowly charged to the suspension over approximately 1 h at 55° C. The slurry was slowly cooled to 20° C. over 4 h. The resulting solid was collected by filtration and washed with a 1:1 (v/v) mixture of acetonitrile and water (1.60 L). The product was dried in a vacuum oven under nitrogen at 70° C. to provide 358 g (69% yield) of (R)-5-bromo-4-(3-(tert-butoxycarbonylamino)piperidin-1-yl)-3-nitro-1H-pyrrolo[2,3-b]pyridine as a yellow solid. $^1$H NMR (600 MHz, DMSO-$d_6$): δ 13.12 (s, 1H), 8.60 (s, 1H), 8.39 (s, 1H), 6.80 (d, J=6.8 Hz, 1H), 3.49 (m, 1H), 3.34 (m, 2H), 3.22 (t, J=11.2 Hz, 1H), 3.00 (t, J=10.2 Hz, 1H), 1.88 (dd, J=12.3, 2.8 Hz, 1H), 1.74 (m, 2H), 1.38 (m, 1H), 1.34 (s, 9H). $^{13}$C NMR (150 MHz, DMSO-$d_6$): δ 154.8, 148.9, 148.2, 147.9, 130.6, 128.5, 113.8, 109.6, 77.6, 54.7, 48.9, 47.3, 30.0, 28.1 (3C), 24.2. HRMS-ESI (m/z): [M+H]$^+$ calcd for $C_{17}H_{23}BrN_5O_4$, 440.0928. found, 440.0912.

Steps 2 and 3: Preparation of (R)-5-bromo-4-(3-(tert-butoxycarbonylamino)piperidin-1-yl)-3-(cyclopropanecarboxamido)-1H-pyrrolo[2,3-b]pyridine To an inserted 1 L pressure reactor were charged (R)-5-bromo-4-(3-(tert-butoxycarbonylamino)piperidin-1-yl)-3-nitro-1H-pyrrolo[2,3-b]pyridine (75.0 g, 1.00 equiv), 1% Pt+2% V/C (11.3 g, 15 wt %), N-methylmorpholine (29.3 g, 1.70 equiv), and 2-MeTHF (750 mL). The reaction mixture was stirred at 50° C. at 5 bar of hydrogen for a minimum of 2 h. Cyclopropanecarbonyl chloride (26.7 g, 1.50 equiv) was charged into the reactor over 10 min at 15° C. The reaction mixture was stirred at 25° C. for 1 h and filtered through Celite. The cake was washed with 2-MeTHF (150 mL). The filtrate was washed with 15 wt % aqueous ammonium chloride solution (450 mL) and water (450 mL) and then distilled in vacuo to ⅓ of it's original volume. Toluene was added to bring the solution back to its original volume. Continuous vacuum distillation was conducted at 55° C. while adding toluene until the 2-MeTHF was below 2 wt %. The resulting solid was isolated by filtration, washed with toluene and dried in a vacuum oven at 40° C. overnight to give 69.8 g (69% corrected yield) of (R)-5-bromo-4-(3-(tert-butoxycarbonylamino)piperidin-1-yl)-3-(cyclopropanecarboxamido)-1H-pyrrolo[2,3-b]pyridine (1:1 toluene solvate) as an off-white solid. $^1$H NMR (600 MHz, THF-$d_8$, 4° C.): δ 10.76 (s, 1H), 9.72 (s, 1H), 8.15 (s, 1H), 7.90 (d, J=2.4 Hz, 1H), 7.18-7.08 (m, 5H), 6.41 (d, J=7.8 Hz, 1H), 3.82 (m, 1H), 3.60 (m, 1H), 3.44 (t, J=10.6 Hz, 1H), 3.30 (dd, J=10.6, 3.9 Hz, 1H), 3.03 (d, J=10.9 Hz, 1H), 2.29 (s, 3H), 2.08 (m, 1H), 1.89 (m, 2H), 1.66 (m, 1H), 1.37 (s, 9H), 1.36 (m, 1H), 0.95-0.80 (m, 4H). $^{13}$C NMR (150 MHz, THF-$d_8$, 4° C.): δ 170.0, 155.8, 149.0, 147.8, 147.6, 138.4, 129.6 (2C), 128.9 (2C), 126.0, 116.6, 115.6, 111.9, 108.8, 78.5, 55.8, 50.2, 49.1, 31.8, 28.6 (3C), 26.3, 21.5, 15.8, 7.70, 7.56. HRMS-ESI (m/z): [M+H]$^+$ calcd for $C_{21}H_{29}BrN_5O_3$, 478.1448. found, 478.1431.

Step 4: Preparation of (R)-5-bromo-4-(3-amino)piperidin-1-yl)-3-(cyclopropanecarboxamido)-1H-pyrrolo[2,3-b]pyridine To an inserted 1 L jacket reactor, equipped with a mechanic stirrer, a nitrogen/vacuum manifold, a thermocouple, and a condenser, were charged (R)-5-bromo-4-(3-(tert-butoxycarbonylamino)piperidin-1-yl)-3-nitro-1H-pyrrolo[2,3-b]pyridine (1:1 toluene solvate) (30.0 g, 1.00 equiv), tetrahydrofuran (180 mL, 6.00 mL/g), followed by 4.5 M sulfuric acid (36.1 mL, 3.00 equiv). The reaction mixture was stirred at 50±5° C. for 2 h and then cooled to 20° C. An aqueous piperazine solution (42.4 g dissolved in 190 mL of water) was added slowly at 25° C. followed by addition of 15.0 mL of sat'd brine. The aqueous bottom layer was removed. The resulting solution was stirred at 20° C. for 5 min. Water (22.0 mL) was added. Continuous distillation was conducted at 50° C. by adjusting the feed rate of ethanol to match the distillation rate until a total of 260 mL of ethanol was added. Water (340 mL) was added at 50° C. over 1 h. The resulting solid was isolated by filtration, washed with 20% ethanol in water (2×60 mL) and dried in a vacuum oven at 50° C. overnight to give 16.4 g (78% corrected yield) of (R)-5-bromo-4-(3-amino)piperidin-1-yl)-3-(cyclopropanecarboxamido)-1H-pyrrolo[2,3-b]pyridine as a light yellow solid. (Note: The proton ($^1$H) and carbon-13 ($^{13}$C) spectra of freebase product are very broad. Therefore, the spectra shown below are of freebase converted to a bis-HCl salt.) $^1$H NMR (300 MHz, DMSO-$d_6$): δ 11.98 (br, 1H), 9.78 (s, 1H), 8.44 (br, 3H), 8.25 (s, 1H), 7.45 (d, J=2.4 Hz, 1H), 3.57 (m, 1H), 3.43 (m, 1H), 3.41 (m, 1H), 3.28 (m, 1H), 3.14 (m, 1H), 2.15 (m, 1H), 1.90 (penta, J=6.5 Hz, 1H), 1.81 (m, 1H), 1.72 (m, 1H), 1.52 (m, 1H), 0.83 (m, 4H). $^{13}$C NMR (75 MHz, DMSO-$d_6$): δ 172.9, 149.5, 145.9, 145.1, 121.9, 114.2, 113.1, 107.8, 53.8, 51.1, 47.5, 28.6, 24.37, 14.7, 7.55, 7.45. HRMS-ESI (m/z): [M+H]$^+$ calcd for $C_{16}H_{21}BrN_5O$, 378.0924. found, 378.0912.

Example 2

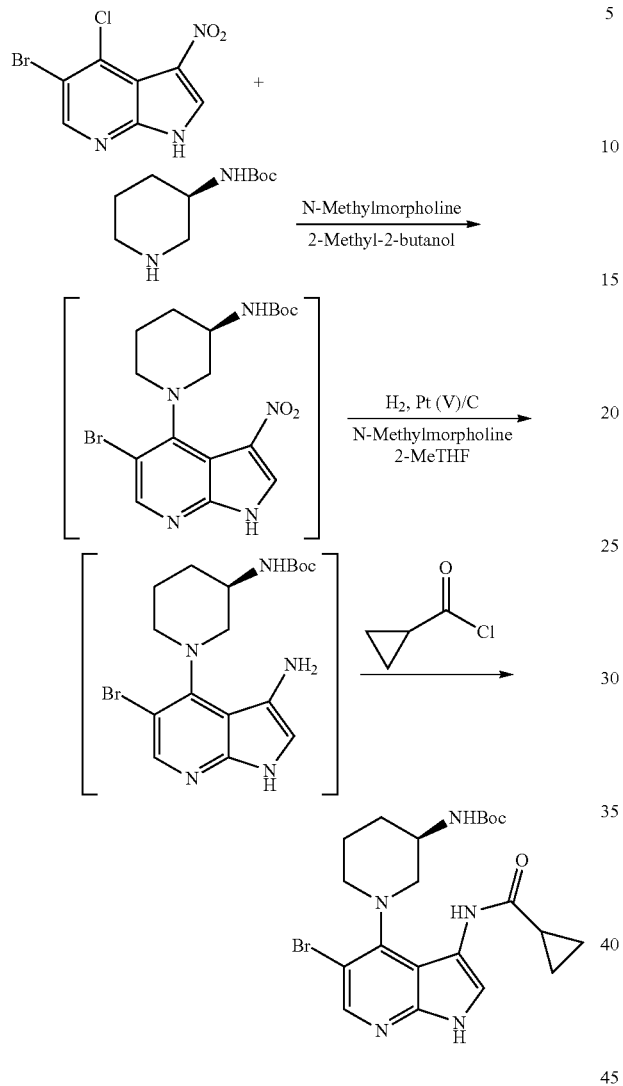

Alternatively, the compound (R)-5-bromo-4-(3-(tert-butoxycarbonylamino)piperidin-1-yl)-3-(cyclopropanecarboxamido)-1H-pyrrolo[2,3-b]pyridine can be prepared from 5-bromo-4-chloro-3-nitro-1H-pyrrolo[2,3-b]pyridine and (R)-tert-butyl piperidin-3-ylcarbamate via a through process without isolating (R)-5-bromo-4-(3-(tert-butoxycarbonylamino)piperidin-1-yl)-3-nitro-1H-pyrrolo[2,3-b]pyridine. The changes to existing procedure are shown as below: The solution of (R)-5-bromo-4-(3-(tert-butoxycarbonylamino)piperidin-1-yl)-3-nitro-1H-pyrrolo[2,3-b]pyridine was hydrogenated directly in 2-methyl-2-butanol after aqueous washes with 15 wt % citric acid aqueous solution (10.0 g/g) and water (10.0 g/g). The solution concentration in 2-methyl-2-butanol was determined by HPLC weight assay.

What is claimed is:

1. A process for preparing (R)-5-bromo-4-(3-amino)piperidin-1-yl)-3-(cyclopropanecarboxamido)-1H-pyrrolo[2,3-b]pyridine of Formula (I):

(I)

or a pharmaceutically acceptable salt thereof, comprising the step of reacting a compound of Formula (II):

(II)

wherein X is I, Cl, or Br, with a compound of Formula (III):

(III)

wherein R is an amino protecting group selected from the group consisting of: triphenylmethyl (trityl), tert-butyloxycarbonyl (Boc), carboxybenzyl (Cbz), trifluoroacetyl and acetyl,
to provide a compound of Formula (IV):

(IV)

subjecting a compound of Formula (IV) to a nitro reduction to obtain a compound of Formula (V):

(V)

reacting a compound of Formula (V) with a compound of Formula (VI):

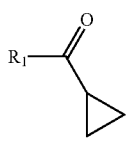

(VI)

wherein R¹ is selected from the group consisting of chlorine, fluorine, bromine, and OR²,
wherein R² is selected from the group consisting of cyclopropylcarbonyl, isobutylcarbonyl, isopropylcarbonyl, ethylcarbonyl, methylcarbonyl, 2-pyridyl, and N-succinimidyl, to obtain a compound of Formula (VII):

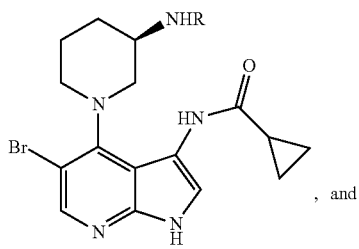

(V), and removing the protecting group R in the compound of Formula (VII) to provide the compound of Formula (I), or a pharmaceutically acceptable salt thereof.

2. The process of claim 1, wherein X is Cl or Br.
3. The process of claim 2, wherein X is Cl.
4. The process of claim 1, wherein the reaction is performed in an organic solvent.
5. The process of claim 4, wherein the organic solvent is selected from the group consisting of alcohols, dimethyl sulfoxide (DMSO), dimethylformamide (DMF), dimethylacetamide (DMA), N-methyl-2-pyrrolidone (NMP), sulfolane, acetonitrile, and propionitrile.
6. The process of claim 5, wherein the alcohol is selected from the group consisting of as 2-methyl-2-butanol, 1-butanol, 2-butanol, 2-methyl-2-propanol, 1-propanol and 2-propanol.
7. The process of claim 6, wherein the alcohol is 2-methyl-2-butanol.
8. The process of claim 1, wherein the reaction is performed with a base selected from the group consisting of N-methylmorpholine, 1,4-diazabicyclo[2.2.2]octane (DABCO), triethylamine, N,N-diisopropylethylamine (DIEA), tetramethylethylenediamine (TMEDA), sodium carbonate, potassium carbonate, cesium carbonate, and potassium phosphate.
9. The process of claim 8, wherein the base is N-methylmorpholine.
10. The process of claim 1, wherein the nitro reduction step is performed using hydrogen, sulfide, or borane as the reductant.
11. The process of claim 10 wherein the nitro reduction step is performed with a platinum or Raney nickel catalyst.
12. The process of claim 11, wherein the catalyst is used in conjunction with a modifier selected from the group consisting of vanadium, iron and copper.
13. The process of claim 10, wherein the nitro reduction step is performed with a base selected from the group consisting of N-methylmorpholine, 1,4-diazabicyclo[2.2.2]octane (DABCO), triethylamine, N,N-diisopropylethylamine (DIEA), and tetramethylethylenediamine (TMEDA).

14. The process of claim 10, wherein the nitro reduction step is performed in a solvent selected from 2-methyl-2-butanol, 1-butanol, 2-butanol, 2-methyl-2-propanol, 1-propanol, 2-propanol, 2-methyltetrahydrofuran, and tetrahydrofuran.

15. The process of claim 1, wherein the amino protecting group R is tert-butyloxycarbonyl (Boc).

16. The process of claim 15, wherein removal of the amino protecting group R is performed under acidic conditions using sulfuric acid, hydrochloric acid, or trifluoroacetic acid.

17. The process of claim 16, further comprising the step of treating a sulfuric acid, hydrochloric acid, or trifluoroacetic acid salt of (R)-5-bromo-4-(3-(amino)piperidin-1-yl)-3-(cyclopropanecarboxamido)-1H-pyrrolo[2,3-b]pyridine Formula (I) with a base selected from the group consisting of sodium hydroxide, potassium hydroxide, potassium phosphate, piperazine, piperidine, pyrrolidine, 1,4-diazabicyclo[2.2.2]octane (DABCO), triethylamine, N,N-diisopropylethylamine (DIEA), and tetramethylethylenediamine (TMEDA).

18. A process for preparing a compound of Formula (IV) or a salt thereof:

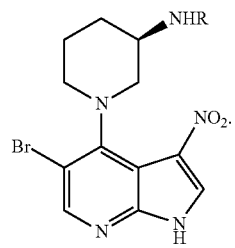

(IV)

wherein R is an amino protecting group selected from the group consisting of: triphenylmethyl (trityl), tert-butyloxycarbonyl (Boc), carboxybenzyl (Cbz), trifluoroacetyl and acetyl, comprising reacting a compound of Formula (II):

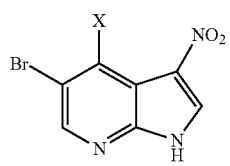

(II)

wherein X is wherein X is I, Cl, or Br, with a compound of Formula (III):

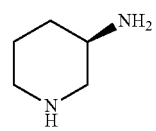

(III)

to provide the compound of Formula (IV) or a salt thereof.
19. The process of claim 18, wherein X is Cl or Br.
20. The process of claim 18, wherein X is Cl.

* * * * *

UNITED STATES PATENT AND TRADEMARK OFFICE
CERTIFICATE OF CORRECTION

PATENT NO. : 10,329,288 B2
APPLICATION NO. : 14/913635
DATED : June 25, 2019
INVENTOR(S) : Chong Han et al.

Page 1 of 1

It is certified that error appears in the above-identified patent and that said Letters Patent is hereby corrected as shown below:

In the Claims

Column 22, Lines 55-65, Claim 1, delete the following structure:

" 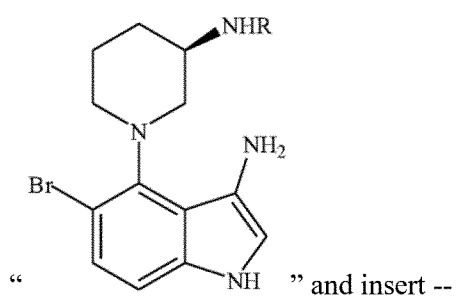 " and insert -- 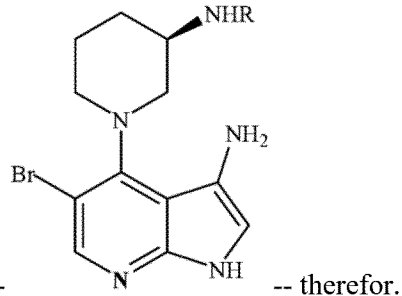 -- therefor.

Signed and Sealed this
Fifth Day of November, 2019

Andrei Iancu
*Director of the United States Patent and Trademark Office*